(12) United States Patent
Goldberg et al.

(10) Patent No.: US 6,312,426 B1
(45) Date of Patent: *Nov. 6, 2001

(54) METHOD AND SYSTEM FOR PERFORMING PLATE TYPE RADIOFREQUENCY ABLATION

(75) Inventors: S. Nahum Goldberg, Brookline; Kenneth K. Tanabe, Cambridge; William J. Rittman, III, Lynnfield; Eric R. Cosman, Belmont, all of MA (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/866,765

(22) Filed: May 30, 1997

(51) Int. Cl.[7] ..................................... A61B 18/04
(52) U.S. Cl. ................. 606/33; 606/48; 606/51
(58) Field of Search ................. 606/35, 37, 38, 606/48, 49, 50, 51, 52, 45, 205, 33, 47

(56) References Cited

U.S. PATENT DOCUMENTS

| | | |
|---|---|---|
| 2,047,535 | 7/1936 | Wappler . |
| 2,828,747 | 4/1958 | August . |
| 3,598,108 | 8/1971 | Jamshidi . |

(List continued on next page.)

FOREIGN PATENT DOCUMENTS

| | | |
|---|---|---|
| 24 07 559 | 8/1975 | (DE) . |
| 195 00 691 | 6/1996 | (DE) . |
| 0040658 | * 5/1980 | (EP) ........................................ 606/35 |
| 0246350A1 | 11/1987 | (EP) . |

(List continued on next page.)

OTHER PUBLICATIONS

Goldberg, S. Nahum, et al., "Tissue Ablation with Radiofrequency: Effect of Probe Size, Gauge, Duration, and Temperature on Lesion Volume," *Acad Radiol*, May 1995; vol. 2; No. 5; pp. 399–404 (Article)

Cosman, Eric R., Ph.D., et al., "Theoretical Aspects of Radiofrequency Lesions in the Dorsal Root Entry Zone," *Neurosurgery*, Dec. 1984; Vol. 15; No. 6; pp. 945–950 (Article).

(List continued on next page.)

*Primary Examiner*—David O. Reip
*Assistant Examiner*—Julain W. Woo

(57) ABSTRACT

A method and apparatus for inducing large volume heat ablations of tissue in a patient involving electrodes that are in contact with the patient's external surface or the surface of an internal organ. A high frequency signal or output from a generator is applied to the tissue near the area electrodes by connection of the generator to the electrodes. Various applications and configurations of electrodes and temperature monitoring are appropriate for different clinical needs and thermal distributions. The use for interoperative ablation of a tumor site within an internal organ or for ablation of a tumor from electrodes placed on the surface of the patient provides a clinical advantage.

62 Claims, 3 Drawing Sheets

U.S. PATENT DOCUMENTS

| | | |
|---|---|---|
| 3,685,518 | 8/1972 | Beuerle et al. . |
| 3,698,394 | 10/1972 | Piper et al. . |
| 3,828,780 | 8/1974 | Morrison, Jr. . |
| 3,845,771 * | 11/1974 | Vise ................... 606/49 |
| 3,890,977 | 6/1975 | Wilson . |
| 3,902,494 | 9/1975 | Haberlen et al. . |
| 3,920,021 | 11/1975 | Hiltebrandt . |
| 3,942,530 | 3/1976 | Northeved . |
| 3,943,932 | 3/1976 | Woo . |
| 3,980,861 | 9/1976 | Fukunaga . |
| 3,982,542 | 9/1976 | Ford et al. . |
| 4,051,855 | 10/1977 | Schneiderman . |
| 4,074,718 | 2/1978 | Morrison, Jr. . |
| 4,184,492 | 1/1980 | Meinke et al. . |
| 4,196,734 | 4/1980 | Harris . |
| 4,204,549 | 5/1980 | Peglione . |
| 4,301,802 | 11/1981 | Poler . |
| 4,311,143 | 1/1982 | Komiya . |
| 4,397,314 | 8/1983 | Vaguine . |
| 4,411,266 | 10/1983 | Cosman . |
| 4,494,539 | 1/1985 | Zenitani et al. . |
| 4,524,770 | 6/1985 | Orandi . |
| 4,532,924 | 8/1985 | Auth et al. . |
| 4,565,200 | 1/1986 | Cosman . |
| 4,608,977 | 9/1986 | Brown . |
| 4,644,955 | 2/1987 | Miocluski . |
| 4,662,368 | 5/1987 | Hussein et al. . |
| 4,662,383 | 5/1987 | Sogawa et al. . |
| 4,682,596 | 7/1987 | Bales et al. . |
| 4,712,559 | 12/1987 | Turner . |
| 4,754,757 * | 7/1988 | Feucht ................... 606/35 |
| 4,796,640 | 1/1989 | Webley . |
| 4,823,791 | 4/1989 | D'Amelio et al. . |
| 4,832,024 | 5/1989 | Boussignac et al. . |
| 4,846,196 | 7/1989 | Wiksell et al. . |
| 4,907,589 | 3/1990 | Cosman . |
| 4,927,420 | 5/1990 | Newkirk et al. . |
| 4,961,435 | 10/1990 | Kitagawa et al. . |
| 4,966,597 | 10/1990 | Cosman . |
| 4,989,608 | 2/1991 | Ratner . |
| 4,993,430 | 2/1991 | Shimoyama et al. . |
| 5,029,588 | 7/1991 | Yock et al. . |
| 5,097,835 | 3/1992 | Putz . |
| 5,099,846 | 3/1992 | Hardy . |
| 5,103,804 | 4/1992 | Abele et al. . |
| 5,116,333 | 5/1992 | Beane . |
| 5,151,102 | 9/1992 | Kamiyama et al. . |
| 5,191,883 | 3/1993 | Lennox et al. . |
| 5,196,009 | 3/1993 | Kirwan, Jr. . |
| 5,197,466 | 3/1993 | Morchosky et al. . |
| 5,220,927 | 6/1993 | Astrahan . |
| 5,249,585 | 10/1993 | Turner . |
| 5,263,931 | 11/1993 | Miller . |
| 5,267,994 | 12/1993 | Gentelia et al. . |
| 5,281,213 | 1/1994 | Milder et al. . |
| 5,281,215 | 1/1994 | Milder . |
| 5,281,218 | 1/1994 | Imran . |
| 5,284,144 | 2/1994 | Delannoy et al. . |
| 5,300,080 | 4/1994 | Clayman et al. . |
| 5,323,778 | 6/1994 | Kardarpa et al. . |
| 5,323,779 | 6/1994 | Hardy et al. . |
| 5,327,884 | 7/1994 | Hardy et al. . |
| 5,330,517 | 7/1994 | Mordon et al. . |
| 5,330,518 | 7/1994 | Nielson et al. . |
| 5,334,193 | 8/1994 | Nardella . |
| 5,342,357 | 8/1994 | Nardella . |
| 5,348,554 | 9/1994 | Imran et al. . |
| 5,370,675 | 12/1994 | Edwards et al. . |
| 5,383,876 | 1/1995 | Nardella . |
| 5,383,917 | 1/1995 | Desai et al. . |
| 5,395,362 | 3/1995 | Sacharoff et al. . |
| 5,403,311 | 4/1995 | Abele et al. . |
| 5,409,000 | 4/1995 | Imran . |
| 5,409,006 | 4/1995 | Buchholtz et al. . |
| 5,409,453 | 4/1995 | Lundquist . |
| 5,433,739 | 7/1995 | Sluijter et al. . |
| 5,443,463 * | 8/1995 | Stern et al. ................... 606/51 |
| 5,458,596 | 10/1995 | Lax et al. . |
| 5,458,597 | 10/1995 | Edwards et al. . |
| 5,462,521 | 10/1995 | Brucker et al. . |
| 5,470,309 | 11/1995 | Edwards et al. . |
| 5,480,417 | 1/1996 | Hascoet et al. . |
| 5,486,161 | 1/1996 | Lax et al. . |
| 5,503,150 | 4/1996 | Evans . |
| 5,520,684 | 5/1996 | Imran . |
| 5,540,684 * | 7/1996 | Hassler, Jr. ................... 606/51 |
| 5,542,915 | 8/1996 | Edwards et al. . |
| 5,545,161 | 8/1996 | Imran . |
| 5,571,147 | 11/1996 | Sluijter et al. . |
| 5,599,294 | 2/1997 | Edwards et al. . |
| 5,599,346 | 2/1997 | Edwards et al. . |
| 5,605,539 | 2/1997 | Buelna et al. . |
| 5,628,770 | 5/1997 | Thome et al. . |
| 5,647,361 | 7/1997 | Damadian . |
| 5,647,871 * | 7/1997 | Levine et al. ................... 606/45 |
| 5,672,173 | 9/1997 | Gough et al. . |
| 5,733,316 | 3/1998 | Tierney et al. . |
| 5,735,847 | 4/1998 | Gough et al. . |
| 5,755,754 | 5/1998 | Rudie et al. . |
| 5,766,169 | 6/1998 | Fritzsch et al. . |
| 5,807,395 | 9/1998 | Mulier et al. . |
| 5,817,092 | 10/1998 | Behl . |
| 5,849,011 | 12/1998 | Jones et al. . |
| 5,855,576 | 1/1999 | LeVeen et al. . |
| 5,873,877 | 2/1999 | McGaffigan et al. . |

FOREIGN PATENT DOCUMENTS

| | | |
|---|---|---|
| 0310431A2 | 4/1989 | (EP) . |
| A0310431 | 5/1989 | (EP) . |
| 0386246A | 9/1990 | (EP) . |
| 0608609A2 | 8/1994 | (EP) . |
| 2 658 424 | 8/1991 | (FR) . |
| 2 659 017 | 9/1991 | (FR) . |
| 2242132 | 9/1991 | (GB) . |
| 1391626 | 4/1988 | (SU) . |
| WO85/01213 | 3/1985 | (WO) . |
| WO94/00188 | 1/1994 | (WO) . |
| WO94/28809 | 12/1994 | (WO) . |
| WO96/04860 | 2/1996 | (WO) . |
| WO96/18349 | 6/1996 | (WO) . |
| WO96/29946 | 10/1996 | (WO) . |
| WO96/37158 | 11/1996 | (WO) . |
| WO96/39914 | 12/1996 | (WO) . |
| WO97/13550 | 4/1997 | (WO) . |
| WO98/27881 | 7/1998 | (WO) . |

OTHER PUBLICATIONS

Goldberg, S. Nahum, et al., "Tissue Ablation with Radiofrequency: Effect of Probe Size, Gauge, Duration, and Temperature on Lesion Volume," Acad Radiol, May 1995; vol. 2; No. 5; pp. 399–404.

Cosman, Eric R., Ph.D., et al., "Theoretical Aspects of Radiofrequency Lesions in the Dorsal Root Entry Zone," Neurosurgery, Dec. 1984; vol. 15; No. 6; pp. 945–950.

Salkoff, L., et al., "Temperature–Induced Seizure and Frequency–Dependent Neuromuscular Block in a TS Mutant Drosophilia," Nature (UK), May 11, 1978, vol. 273, No. 5658, pp. 156–158.

Guttman, R., et al., "Squid Axon Membrane Response to White Noise Stimulation," *Biophysical Journal*, Dec., 1974; vol. 14, No. 12; pp. 941–955.

Cosman, E.R., et al., "Methods of Making Nervous Systems Lesions," *Neurosurgery*, vol. 3, 1984; pp. 2490–2499.

Tew, et al., "The Treatment of Trigeminal Neuralgia by Percutaneous Radiofrequency Technique", *Clinical Neuro*, pp. 557–578, 1977.

Tew, et al., "Application of Stereotactic Principles to the Treatment of Trigeminal Neuralgia", *Appl. Neurophysiol.* 41:146–156, 1978.

McGahan, John P., et al., "Percutaneous Ultrasound–Guided Radiofrequency Electrocautery Ablationn of Prostate Tissue in Dogs," *Acad. Radiol.*, 2:61–65, 1995.

Solbiati, Luigi, et al., "Percutaneous US–guided Radio–Frequency Tissue Ablation of Liver Metastases: Treatment and Follow–up in 16 Patients", *Radiology*, 202:195–203, 1997.

Levin, Allan B., "Thermocouple–monitored Cordotomy Electrode", *J. Neurosurg*, 53:266–268, 1980.

Tobler, William D., et al., "Improved Outcome in the Treatment of Trigeminal Neuralgia by Percutaneous Stereotactic Rhizotomy with a New, Curved Tip Electrode", *J. Neurosurg.*, vol. 12, No. 3, pp. 313–317, 1983.

Tew, John M., Jr., et al., "A 10–Year Experience in the Treatment of Trigeminal Neuralgia: A Comparison of Percutaneous Stereotaxic Rhizotomy and Posterior Fossa Exploration", *Clinical Neurosurgery*, vol. 24, pp. 557–578.

Goldberg, S. Nahum, "Radiofrequency Tissue Ablation: Increased Lesion Diameter with a Perfusion Electrode", *Acad. Radiol.*, 3:636–644, 1996.

Goldberg, S. Nahum, et al., "Tissue Ablation with Radiofrequency: Effect of Probe Size, Gauge, Duration, and Temperature on Lesion Volume," *Acad Radiol*, May 1995; vol. 2; No. 5; pp. 399–404.

* cited by examiner

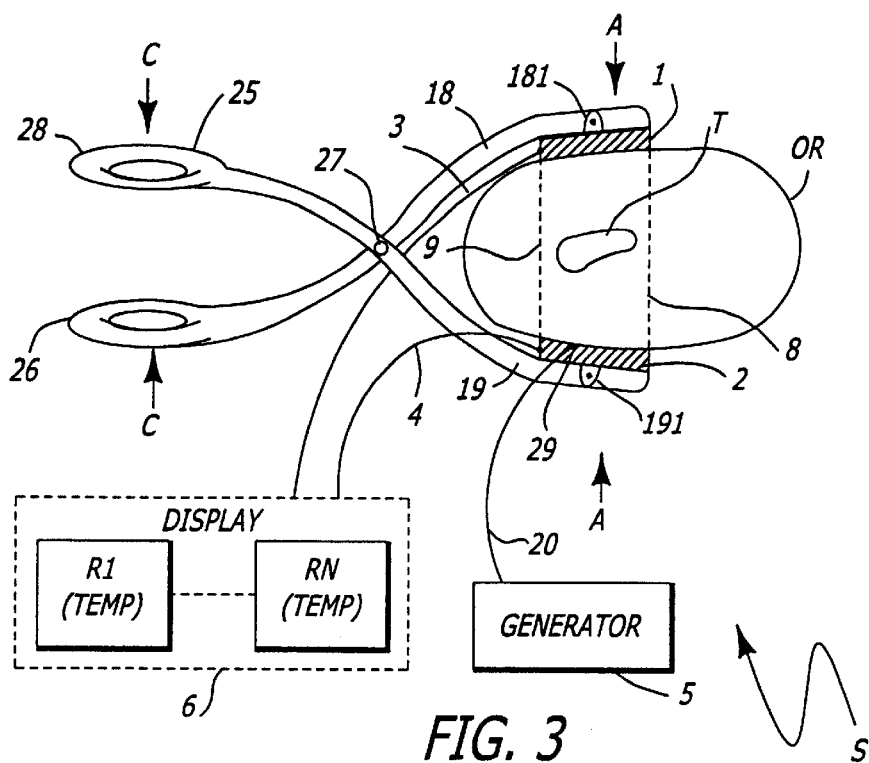
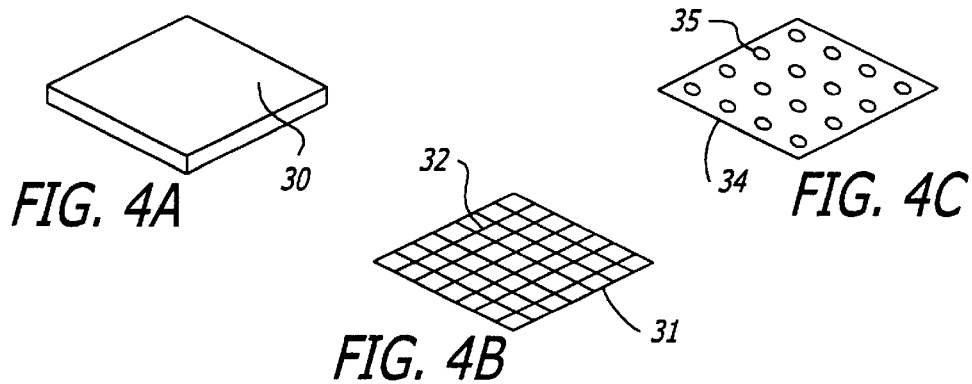
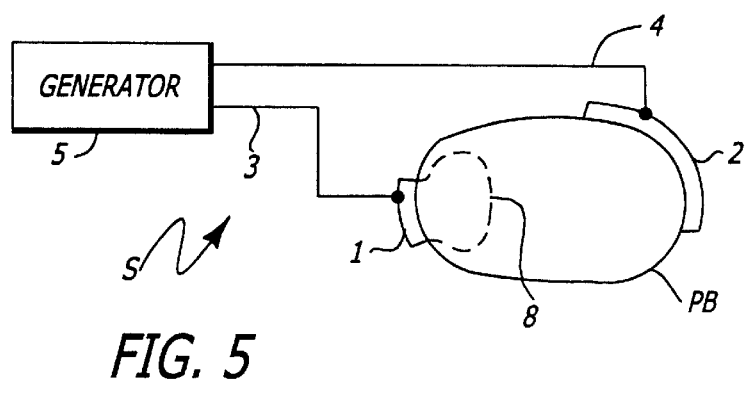

METHOD AND SYSTEM FOR PERFORMING PLATE TYPE RADIOFREQUENCY ABLATION

FIELD OF THE INVENTION

This invention relates generally to advances in medical systems and procedures for prolonging and improving human life. More particularly, this invention relates to an improved system and method including radiofrequency applicators of area or array type configuration for performing ablation of volumes or masses of abnormal tissue, such as tumors.

BACKGROUND OF THE INVENTION

The use of electrodes for performing radiofrequency ablation on certain parts of a patient's body is well known. Conventional electrodes are typically elongated, cylindrical shafts with insulation over a portion of the shaft. Such electrodes typically have an exposed, conductive tip, which is used to contact body tissue in a region where a heat lesion or ablation zone is desired.

In conjunction with such conventional electrodes, in most applications, large area or plate type electrodes are also commonly used to serve as reference electrodes. Such reference electrodes are placed external to a patient's body and never heated, but merely serve as a return path for the radiofrequency (rf) current circuit. These reference electrodes typically have a greater surface area than the surface area of radiofrequency (rf) ablation electrodes.

As a result of their greater surface areas, such reference electrodes spread or dissipate the radiofrequency current over a wide area of the tissue and consequently, prevent concentrated heating at any one point. Such reference electrodes are deliberately configured to remain cool as a safety precaution, to avoid burning surface tissue on a patient's body. To operate both the radiofrequency (rf) ablation electrode and reference electrode, they are connected to a radiofrequency generator, which provides the recurring current and voltage to produce the heat ablation around the conductive tip of radiofrequency (rf) ablation electrode. Such systems and techniques are described in many articles, as for example, a research paper by Cosman, et al., entitled "Theoretical Aspects of Radiofrequency Lesions in the Dorsal Root Entry Zone," *Neurosurgery*, December 1984, Vol. 15, No. 6, page 945–950. There are several types of radiofrequency equipment available, as for example, the electrodes and generators from Radionics, Inc., located in Burlington, Mass. In the research paper by Cosman, et al., a generally thin cylindrical ablation electrode is inserted into the body, and heating is enabled near it. The reference electrode, which is typically an area electrode, is placed on the patient's skin. The reference electrode specifically is much larger in surface area (for example, 150 square centimeters) than the thin cylindrical ablation electrode so that no substantial heating occurs near the reference electrode. Any such heating at the area electrode would cause skin burns, which is contrary to the radiofrequency technique described in the paper by Cosman, et al., referenced above.

Cylindrical electrodes are also commonly used for some applications. Cylindrical electrodes are typically metal tubes of 1 to 3 millimeters in diameter and several centimeters in length.

Typically, concentration of heat is maximum near the exposed conductive tip of the cylindrical electrode, with it progressively decreasing as the distance from the exposed tip increases. The degree of heat distribution depends on the radiofrequency current density in the tissue and electrical and thermal conductivities of the tissue near the electrode. Further details are discussed in the research paper by Cosman, et al., referenced above. Cooled radiofrequency electrodes can deposit heat at greater distances from the point at which the electrodes are placed. Yet, temperature inhomogeneities or hot spots can develop near the radiofrequency electrode, and this can lead to dangerous and uncontrolled boiling, charring, sticking, explosive steam formation, and hemorrhaging. This limits the amount of power that can be deposited into the tissue, limiting therefore, the volume of coagulated tissue.

Different techniques for ablation of cancerous tumors in the liver, brain, and elsewhere by use of such cylindrical, tubular, radiofrequency electrodes introduced into or near the tumor site, are discussed in a research paper by Cosman, et al., referenced above, as well as a research paper by Goldberg, et al., entitled "Tissue Ablation With Radiofrequency: Effect of Probe Size, Gauge, Duration, and Temperature on Lesion Volume," *Acad. Radio.*, 1995, Vol. 2, No. 5, Pages 399–404. Carefully targeting the tumor site with the electrode is sometimes necessary, which requires stereotactic methods or iterative imaging of the patient's body while placing the electrode within the patient's body. Imaging can be performed by using ultrasound, CT, MRI, X-ray, or other techniques. If a tumor exists in the soft tissue of a limb, torso, neck, etc., and is rather large, it is difficult to determine the exact location in the tumor where the radiofrequency electrodes should be planted for ablation purposes. Thus, using discrete, cylindrical, radiofrequency electrodes in such cases, whether interoperatively or percutaneously, is not simple, and typically requires considerable imaging and careful planning prior to performing a procedure. By way of example, for large tumors, in an internal organ such as the liver, it is almost impossible for a surgeon, without use of sophisticated equipment to assist with targeting the desired location, to determine the exact location and size of the tumors.

Open surgical resection of a large sector of the liver is done routinely to remove regions where cancerous tumors are believed to exist. Such a procedure is possible only after using imaging techniques to determine the exact locations where the cancerous tumors are believed to exist. Such operations are technically challenging, morbid, and dangerous, often resulting in fatalities. They require an expensive and time-consuming surgical procedure. For a person in frail health or with significant health problems, undergoing such major surgery can be prohibitive or lead to extended recovery periods, which are inconvenient and costly.

Another known form of electrosurgery is often referred to as bipolar electrocautery or bipolar coagulation. To perform this procedure, a surgeon typically uses bipolar forceps, which are similar to surgical forceps, except that each arm of the forceps is insulated from the other and connected to a high frequency power source. Such bipolar forceps and coagulators are available from Radionics, Inc., located in Burlington, Mass. Such forceps typically have very small tips, which are conductive and therefore, serve as electrodes, contacting small volumes of tissue between them. Such tips typically have an area of no more than 4 to 6 square millimeters or 0.04 to 0.06 square centimeters. The purpose of these devices is to coagulate small volumes of tissue between the tips when the forceps are applied to the tissue and high frequency current is passed between the tips and through the tissue.

A common application where such forceps may be used is for purposes of coagulating small blood vessels or to stop bleeding during surgery. Often, the tissue that is coagulated can boil and char because of the very focused heat, which is caused by the small area forceps tips and the high density of coagulating current running through the tissue between them. Such small area tips would not be adequate to coagulate larger volumes of tissue lying within an organ or limb. For example, common dimensions for a tumor in the liver are typically between 1 centimeter and 6 centimeters or more. A tumor, whose size exceeds 1 centimeter would be too large to coagulate by using small area tip bipolar forceps of the type described above. If such bipolar forceps are in fact used, only tissue volumes of less than one cubic centimeter could be coagulated. Hence, this makes such forceps impractical for coagulating large tissue volumes, especially those exceeding 1 cubic centimeter in size, which is often desirable for minimally invasive procedures involving heat coagulation of tumors within organ or limb tissues. Moreover, use of small area bipolar forceps often result in inhomogeneities in heat distributions and uncontrolled hot spots or charring of tissue. Such side effects make their use for larger tissue volumes impractical and unsafe.

A less invasive system or method of ablating large volumes of tissue having cancerous areas would be desirable. A method and system, which is minimally invasive in terms of penetrating large tissue volumes, either through intact skin or interoperatively, and which would avoid heat inhomogeneities and hot spots is also desirable.

SUMMARY OF THE INVENTION

The present invention is directed to a system and procedure for using area-like or plate-like electrodes for effecting large volume, uniform, and extended ablation of the tissue areas proximate the plate-like electrodes. In accordance with the present system and procedure, the plate-like electrodes are placed on the surface or boundary layers of body tissue, where the ablation is desired.

In accordance with one embodiment of the present invention, the plate-like electrodes comprise plates configured to lie approximately parallel or opposing each other, such that they make a lesion by coagulating most of the body tissue volume between them. For instance, in the case of performing open surgery on an internal organ, such as a liver, pancreas, lung, or other such organs, which is visualized by imaging techniques, the plate-like radiofrequency electrodes can be simply placed on the surface of such an organ. A radiofrequency current is applied between the plates or through the tissue proximate the plates. This causes a large and relatively uniform distribution of heating within the tissue to ablate the tissue near and between the plates. For example, if a set of nearly parallel radiofrequency (rf) plate-like electrodes are positioned on either side of a tumor volume, a tubular section of tissue volume between the plates can be ablated by radiofrequency heating. The extent of ablation can be increased, to easily encompass the entire tumor and kill it.

The system and procedure in accordance with the present invention has many advantages, one of which is that the surgeon need not determine the precise position of the tumor. Also, as there is no need to penetrate the tissue with radiofrequency electrodes, any danger from a hemorrhage, vessel puncture, and spread of cancer cells within the tissue is avoided.

Soft tissue tumors such as sarcomas often occur in the limbs or torso, and it is desirable to be able to ablate them without inserting electrodes within the body and incurring the risk of hemorrhage.

In accordance with another embodiment of the present invention, radiofrequency plate electrodes may be placed for example, on the surface of the limb near the sarcoma, to cause global heating within the tissue so as to engulf the sarcoma and destroy it.

In accordance with yet another embodiment, area radiofrequency electrodes that are cooled may be used to prevent the surface skin from being destroyed while producing heating deeper in the tissue in order to destroy the tumor volume.

It should be recognized that a variety of electrode configurations to give a plate-like or area-like radiofrequency electrodes can be devised, and various electrode applicators can be structured to meet the specific clinical needs.

BRIEF DESCRIPTION OF THE DRAWINGS

Further features and advantages of the invention will become readily apparent from the following specification and from the drawings, in which:

FIG. 3 in accordance with another embodiment of the present invention shows moveable area electrodes in a forceps type configuration;

FIG. 4a, 4b, and 4c show various constructions of area, area-like, or plate-like electrodes in accordance with the present system and process;

FIG. 5 shows another embodiment in accordance with the system and process of the present system.

DESCRIPTION OF SOME PREFERRED EMBODIMENTS OF THE INVENTION

At the outset the papers by Cosman et al., entitled "Theoretical Aspects of Radiofrequency Lesions in the Dorsal Root Entry Zone," and Goldberg et al., entitled "Tissue Ablation With Radiofrequency: Effect of Probe Size, Gauge, Duration, and Temperature on Lesion Volume," mentioned above are incorporated herein by reference.

Figure 1:
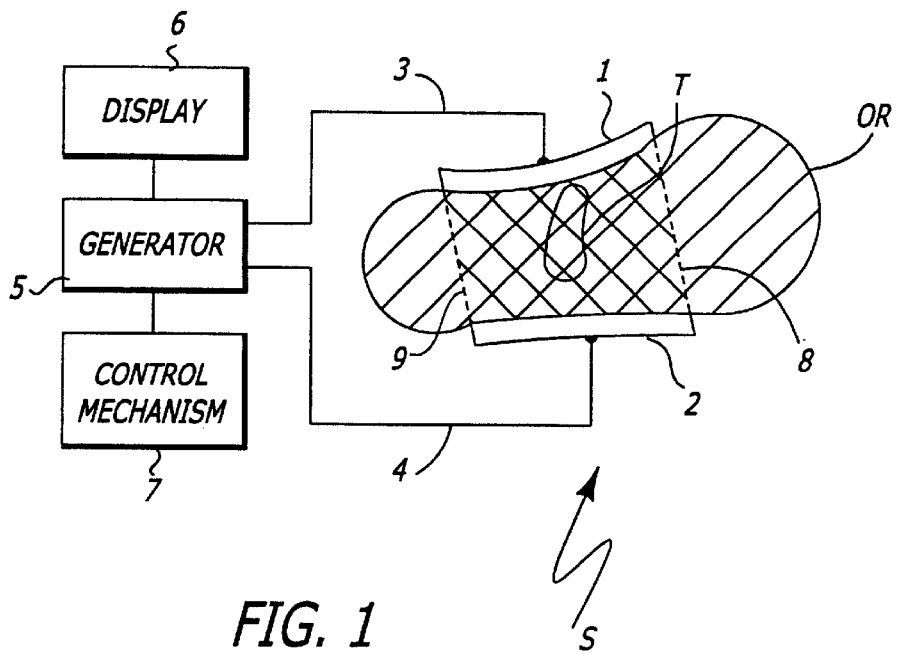
FIG. 1 shows schematically rf area electrodes, to ablate a desired portioned section of a patient's organ, such as a volume or mass of a tumor.

Referring now to FIG. 1, a system S for performing plate type radiofrequency ablation in accordance with the present invention is generally shown. The system S includes area-type electrodes 1 and 2, which are shown in contact with nearly opposing sides of a body organ OR within a desired operative field. The organ OR may be any internal organ in a patient's body such as the liver, pancreas, lungs, heart, etc. Alternatively, the organ OR may be an external organ in a patient's body, such as a limb, torso, head, neck, etc. (not shown). It should be recognized that the organ OR is shown within the patient's body only by way of example. A section of the organ OR, which falls between the area-type electrodes 1 and 2 is illustrated in sectional view by wide diagonally hatched lines.

The area-type electrodes 1 and 2 are connected by wires, cables, or any other electrical connections 3 and 4, respectively, to a generator 5 yielding a high frequency output (voltage, current, or power). The generator 5 may provide some form of a display, indicated by reference numeral 6, to indicate readings corresponding to its electrical outputs. For example, the display 5 may indicate a reading (one of R1 through RN) corresponding to levels of current, voltage, power, impedance, and/or temperature in the event the area-type electrodes 1 and 2 incorporate temperature sensors. The generator 5 also has a control mechanism indicated by reference numeral 7 to control the levels of current, voltage, power, impedance, and/or temperature. The control mechanism may take the form of controls, which may be manually maneuvered to control the levels of power current, voltage, temperature(s) at the electrodes or in the nearby tissue, impedance between the electrodes and so on. Alternatively, the various controls 7 may be automatically controlled. For example, they may be coupled to a feedback of temperature levels, in the event the temperature levels are being monitored at the area-type electrodes 1 and 2 or within the body organ OR. The generator 5, the display 6 and the control mechanism 7 are shown separately for illustration purposes only. The display 6 and the control mechanism 7 may be part of the generator or separate devices.

When the high frequency generator 5 is turned on and a high frequency voltage is applied to the electrodes 1 and 2, the high frequency current passes between the electrodes 1 and 2, and through the organ OR. This causes heating by ionic friction or dielectric heating in the ionic medium of the organ OR. A high frequency generator 5 such as one available from Radionics, Inc., Burlington, Mass. may be used.

Considering the example of FIG. 1, a target tissue volume or area T, which is shown by way of example may be a cancerous tumor or other abnormality which is to be destroyed. To destroy the tissue within the volume or area T, the plate-like electrodes 1 and 2 are disposed on either side of the tissue volume T. By heating the plate-like electrodes 1 and 2, the zone of heat between the electrodes 1 and 2 is created, which engulfs the target T. By way of example, in FIG. 1, the dashed lines 8 and 9 provide a sectional representation of the boundaries of a heat lesion zone created between the plates. Between these perimeters indicated, the tissue may be heated to lethal levels. For example, sustaining tissue at approximately 50 degrees centigrade or higher temperatures for several minutes would kill the tissue. Further details on this are discussed in the papers by Cosman, et al., and by Goldberg, et al., incorporated herein by reference. The heat lesion zone shown by cross-hatched lines in the cross-section of the organ OR in FIG. 1, represents the region where the tissue is destroyed or ablated.

Further as an example of the present invention, considering an open surgical field wherein a surgeon has exposed the liver, as represented by organ OR in FIG. 1. It is common for the surgeon to resect a large portion of the liver to remove a cancerous tumor. This is a technically challenging, highly morbid procedure. Many patients cannot withstand the ordeal of such an operation nor the hospital convalescence which follows. Such surgery takes considerable time and is very expensive as well. By applying the plate-like high frequency electrodes in accordance with the present invention across the liver, a large portion of the liver can be ablated, including that portion which includes the tumor T. There is little or no open surgery performed on the organ OR, and the organ can be kept intact, thus, reducing the risk of hemorrhage and long convalescence. Thus, in one application, interoperative coagulation of internal organs can be performed, which may be exposed during surgery or visualized laproscopically, so as to ablate or to coagulate part or all of the organ without requiring a surgical incision within it.

In a specific illustration of one example of an ablation volume produced in accordance with FIG. 1, circular or square plate electrodes, approximately 2 inches (5 centimeters) in diameter or side length referenced by numerals 1 and 2 are placed on opposite sides organ OR, which in this particular illustration represents a living liver. A radiofrequency generator with a radiofrequency output of about 500 KiloHertz is connected by electrical cables to each of the plate electrodes 1 and 2. A level of power output from the generator 5 of approximately 50 to 100 watts is applied to the tissue between the plates 1 and 2 for several minutes. A cylindrical, prismatic-shaped volume of tissue, indicated between the boundaries 8 and 9 in FIG. 1, is completely coagulated between the electrode plates 1 and 2, and all tissue within that volume is killed. Volumes of 1, 5, 10, 20, or more cubic inches (10 to 400 cubic centimeters) can be coagulated or killed in this way. A post-mortem resection of such in-vivo liver ablations indicates a clean border with minimal indication of hot spots, boiling, or charring. The high frequency generator 5 may be any suitable one, as for example, Model No. RFG-3D available from Radionics, Inc., Burlington, Mass. The high frequency generator 5 can have a power range between zero and several hundred watts. The range of radiofrequency or high frequency can vary. Also, ranges from less than 100 kH to several tens or hundreds of Mega Hertz could be used.

Figure 2:
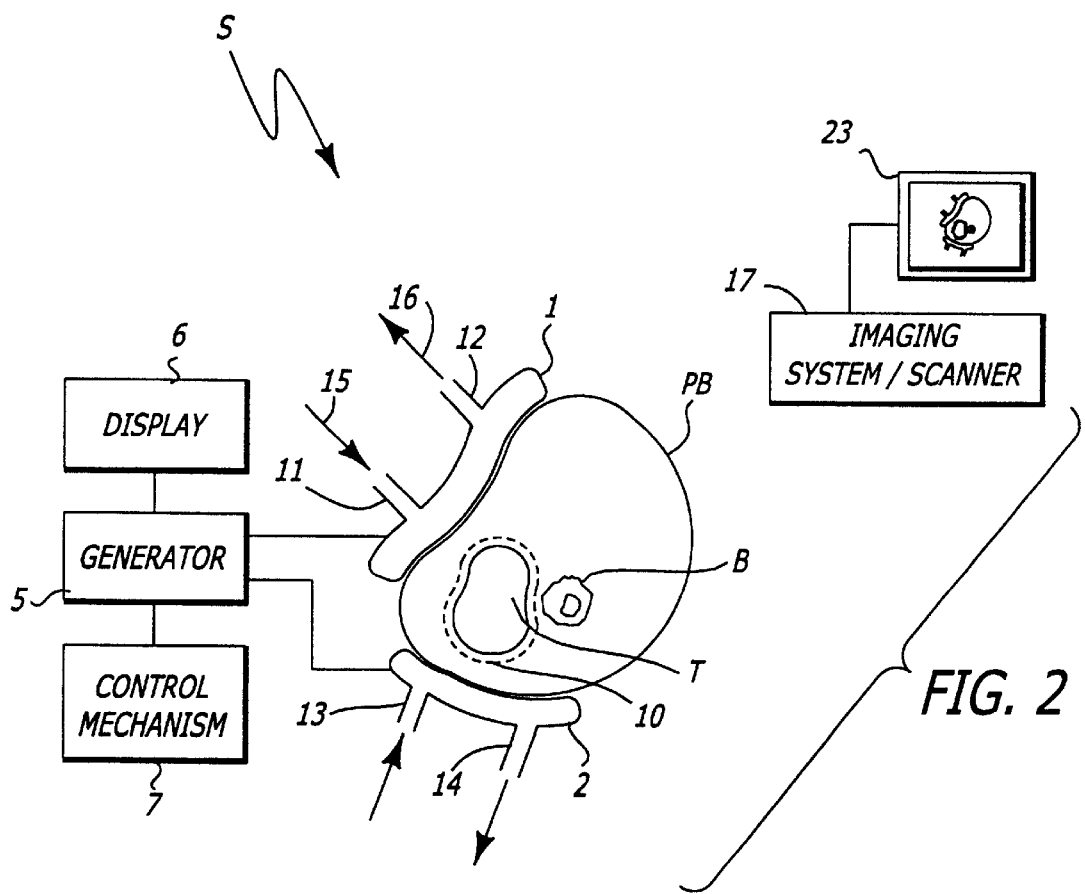
FIG. 2 shows a schematic diagram of cooled area electrodes in accordance with another embodiment of the present system and process placed in contact with a patient's body surface to make a heat ablation.

Referring to FIG. 2, another example of the present invention is shown. An external organ PB, which is part of the patient's anatomy, is shown in sectional view. Inside the organ, bony structures B may exist as shown in FIG. 2. The external organ PB could be a leg, arm, torso, pelvis, or neck. Also shown is a target volume or area T within the organ PB that is to be ablated or destroyed. The surface structure of the organ PB may be skin, which one may not wish to destroy. The electrodes 1 and 2 are placed on the external surface of the organ and connected to the radiofrequency generator 5, in a manner similar to the configuration shown in FIG. 1. Depending on the clinical indications, the electrodes 1 and 2 may have cooling elements within them to prevent excessive heating at the point where the electrodes 1 and 2 contact the external surface of the organ PB. For example, electrode 1 has an inflow tube 11 and outflow tube 12, which can circulate cooled fluid such as chilled saline, indicated by the flow arrows 15 and 16, respectively. The chilled fluid chills the electrode 1, and therefore, the skin surface of the organ PB just below it. Similar inflow and outflow channels 13 and 14 of electrode 2 exchange cooled fluid for the same purpose. In this situation, the electric field lines created by the impression of a radiofrequency voltage across the electrodes 1 and 2, together with the boundary conditions imposed by the cooled electrodes, create an ablation volume somewhat away from the electrodes 1 and 2 and the surface of the organ OR. For example, the dashed line 10 illustrates in sectional perspective the ablation volume.

This may correspond, for example, to the isotherm of temperatures around 50 to 60 degrees centigrade or greater, which may be sustained for several seconds to several minutes to cause tissue death of the ablation volume within line 10. This may be preplanned, calculated, or heuristically determined to engulf the volume T associated with the tumor.

In accordance with the present invention, imaging of the patient anatomy relative to the positioning of electrodes 1 and 2 may be done with ultrasound, CT, MR, or interoperative ultrasonic imaging. Preplanned, three-dimensional treatment planning for such thermal radiofrequency surgery can be carried out in a computer workstation based on data taken from image scanners such as CT, MR, PET, X-ray, ultrasound, etc. Interactive imaging could be present, as indicated by the element 17, which could be a CT, MR, X-ray, PET, ultrasound, or other type of scanner. Its data processing unit could be built in or could be coupled to a computer workstation 23 with a display apparatus, such as a CRT, that can illustrate the sectional or volumetric rendering of the anatomy PB and also the position of the electrodes 1 and 2 and the isotherms such as dashed line 10. The scanner 17 could be positioned in a coordinated way with the position of the electrodes 1 and 2, and thereby to visualize the effect of the thermal lesion on the target volume T in a graphical and stereotactic fashion.

FIG. 3 shows a further embodiment of the present invention wherein the plates 1 and 2 are attached to an articulated forceps-like or tong-like device to grasp an external or internal organ. In this particular embodiment, the arms 18 and 19 are coupled to the electrodes 1 and 2. There is a hinge 27 and there are handles 26 and 27, which when closed in the direction indicated by the arrows C, will clamp the electrodes 1 and 2 onto the organ OR in the direction indicated by the arrows A. There is a target volume T within the range of coagulation of the plates 1 and 2, and the isotherm or kill volume would be bounded as illustrated by the dashed lines 8 and 9 inside the organ OR. Electrical connections 3 and 4 connect to a radiofrequency (rf) generator 5, which connects the radiofrequency output of the generator to the electrodes. That in turn causes the heating of the tissue as discussed above. A thermal sensor 29 might be embedded in one or both of the electrodes 1 and 2. A thermal-sensing, connecting cable 20 connects to the generator 5 so that readings R1 and RN can read out single or plural temperatures associated with one or both of the area electrodes 1 and 2.

A plurality of such temperature sensors may be built in with the area electrodes to monitor surface tissue temperature nearby. Alternatively, temperature sensors may be placed in the tissue near the area electrodes 1 and 2 and monitored on the display 6, which may provide readings R1 through RN to indicate temperature levels. The readings R1 through RN may alternatively indicate other parameters. Various embodiments of the forceps-like applicator shown in FIG. 3 are possible. For example, the hinged structure can be replaced by other articulations. Also, the plates 1 and 2 can also have their own articulations, as for example, use of hinge joints 181 and 191 to connect to the arms 18 and 19, respectively, so as to better conform to the surface of the internal or external body part.

FIG. 4 shows various of the many possible embodiments of geometries of area electrodes in accordance with the present invention. Electrode type 30 could simply be a conductive plate made of metal, conductive plastic, or conductive rubber. Element 31 is shown as a mesh or matrix of conductive wires 32 so as to provide a conforming, lightweight area contact with tissue. Thus, the area-like electrodes may be flexible to conform to the curved shapes of organs. Element 34 is shown as a substrate with an array of conductive elements 35, which could be of any shape, geometry, or multiplicity and distribution on the surface plate 34. Tailored shapes (circles, ellipses, rectangles, oblong shapes, paddles, and the like) of area electrodes could be devised for a particular body part. Different areas of area electrodes could be implemented, depending on the size of the body part, the size of the target area or volume T, the extent of heating, or the particular geometry and considerations of the clinical application. Areas of area electrodes of 0.5 to 100 or 500 square centimeters or larger may be useful for particular organs, tumors, or anatomical sites.

Area electrodes of mesh or wire or discrete element types such as those illustrated by reference numerals 31 or 35 in FIG. 4 may have conductors of a smaller actual conductive element area than the effective total area over which the area electrode contacts the tissue. For instance, the total contact area of the actual wire conductors 32 in the electrode 31 may be only a small percent of the entire area covered by the wire field. However, because the total wire 31 field simulates an equipotential area over the tissue it contacts, it acts effectively like a large area continuous conductive electrode in terms of its heating affect. That is, it has the equivalent heating effect of a continuous metal plate electrode of area equal to the area of 31.

FIG. 5 shows another embodiment of the present invention where different sized electrodes are used to alter the temperature distribution of the rf ablation. In accordance with this embodiment, electrode 1 has a smaller area than electrode 2. In this sectional drawing, through the patient's body element PB, the concentration of current density is higher near the smaller area electrode 1. Thus, the isotherm 8, which may represent, for example, the 50 degree centigrade or the lethal isotherm, is shifted more towards electrode 1 and less towards electrode 2. By tailoring and varying the electrode areas, one can thereby shift the distribution of thermal heating. By placing the area electrodes in different positions on the body, either parallel, opposed, or adjacent to one another, in accordance with the above discussion can also vary the temperature distribution within the tissue.

Figure 6:
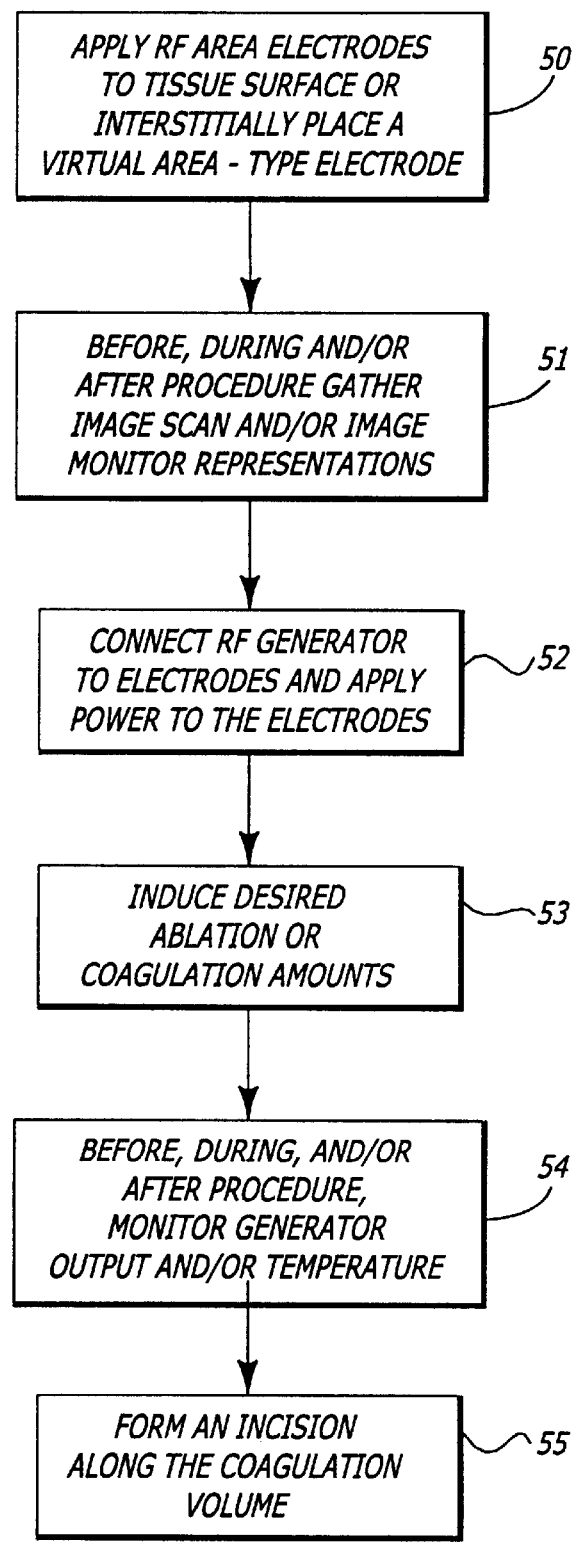
FIG. 6 shows a flow chart of the operation of system and process in accordance with the present invention.

Referring now to FIG. 6, a flow chart is shown to illustrate the procedure of applying area-type radiofrequency electrodes to a patient's anatomy and inducing desired ablations. The procedure starts at block 50, which represents the step of applying the area radiofrequency electrode to the desired surface of the desired organ or to the desired surface of a patient's anatomy. Alternatively, if a multiplicity of linear electrodes are inserted into the organ or anatomy, such a procedure is referred to as "interstitially" placing a virtual area-type electrode.

The steps of inserting such electrodes or placing the electrodes relative to the internal anatomy could be imaged as indicated in block 51 by the imaging system or scanner 17 or monitor 23, such as a CT, MR, X-ray, ultrasound, or other type of imaging scanner. As indicated by block 51, the position of a target volume or area such as a tumor may be imaged even before or after inserting the electrodes or placing them relative to the anatomy. For example, imaging data may be taken during placement of the electrodes or when generating the desired radiofrequency levels to monitor the progress of coagulation. Scanners, such as MR scanners, monitor the process of heating, and thus, may be used during the process of coagulation to observe the extent of ablation.

Operation proceeds to the next step, represented by block 52, in accordance with which the generator 5 is connected to the electrodes 1 and 2 by connection cables. After the electrodes 1 and 2 are connected, the power generated by the generator 5 is applied to the area electrodes 1 and 2. With application of the desired levels of power, the radiofrequency ablation process or coagulation is initiated, as illustrated by block 53, to induce desired ablation or coagulation amounts. At this point, image scan data representations may also be acquired, as represented by block 51.

Before, during, and/or after the procedure, is may be desirable to monitor the generator output parameters, as illustrated by block 54. Also, it may be desirable to monitor temperature levels at the area electrodes or within the tissue to be ablated, in which case, temperature sensors may be included within the electrodes or placed "interstitially." The generator parameters may be analyzed to determine if the desired amount of coagulation is accomplished. This can also be determined by monitoring the image representations, or by monitoring the temperature levels to determine if the appropriate coagulation is reached. At that point, the power from the generator 5 may be turned off and the ablation process terminated.

Another variation of the process in accordance with the present invention would be to use the ablation steps, as shown in FIG. 6, to coagulate tissue and thereby to reduce blood circulation within the tissue preparatory to performing a surgical incision. For example, area electrodes 1 and 2 can be placed on the liver, and a coagulation through the liver can be made according to the above description. When the coagulation is complete, a sectional volume through the liver is coagulated, including many of the arteries and vessels in the tissue. After coagulation, an incision can be made through the coagulated tissue with a reduced amount of bleeding in comparison with the state of tissue before coagulation was made. This is illustrated by step 55, as shown in FIG. 6.

Accordingly, the system and method in accordance with the present invention can therefore be used as an adjunct to performing a surgical incision within a portion of the body to reduce problems of bleeding during surgery.

It should be recognized that the present invention is directed to at least one or two or more area-type or plate-type electrodes to induce ablative heating in a substantial volume proximate the area electrode(s) or in the tissue between the area electrodes. Variations of the geometry, lesion parameters, frequency range, electrode characteristics, and materials can be made in various embodiments in accordance with the present invention. The electrodes can be of a widely varying shape, such as circular, square, or irregular shapes. For a smallest heating volume as near a skin cancer, tumor, or melanoma, an electrode of about 0.5 to 2 square centimeters may be appropriate. For a volume in a limb, hand, foot, pancreas, etc., it may be that electrodes of 1 to 50 square centimeters may be desirable. For larger organs or larger tumors, wherein the tumors of dimensions up to 10 centimeters or more are encountered, the one or more area electrodes with areas of 100 to 1000 square centimeters may be desirable.

Area or "interstitial" electrodes or combinations of them as described above may be useful for certain organs such as breast, liver, pancreas, testicles, abdomen, lung intestines, throat, neck, or limbs. A matrix of electrodes and a plurality of electrodes may be used to achieve heating patterns according to clinical needs. Area electrodes consisting of a plurality of discrete electrode points or small surface-penetrating electrode needles may be considered for better contact with the internal organ. Electrodes can be fabricated from various conductive materials including metal, carbon structures, metal-impregnated plastics or rubbers, screens of stainless steel, titanium, platinum, or other conductive, biocompatible materials.

The area electrodes can be configured for one-time use or to be reused and re-sterilized. If they are configured for a single use, they may be easily disposed and there is no need for sterilization before further use. This has the advantage of reducing the risk of transmission of diseases, such as AIDS and of reducing expenses with cleaning and resterilizing. In addition, the area electrodes may be for surface contact during surgery or external application, or they may be implanted within the body for a period of time for continuous re-application of heat.

The area electrode can have a multiplicity of segmented conductive areas so as to provide a matrix or patchwork of conductive structures so that the generator can distribute the potential to each of these various structures in different ways during the procedure to achieve different heating patterns. Such heating patterns, for example, could be achieved by electrifying the elements 35 in FIG. 4 in independent ways with multiplexing the output from a generator such as generator 5. By MRI imaging, such as image scanner 17 in FIG. 2, real-time visualization of the thermal distribution may be achieved on the display 23, and variations of the potential on the electrode or portions of the electrode may be made to achieve different temperature distributions under real-time visualization.

Various high frequency generators can be used with a plurality of temperature monitors, measuring temperature at a multiplicity of points on the area electrode or within the bodily tissue itself with independent temperature sensors in a variety of displays of rf high frequency parameters. Cooling pumps can be connected cooperatively with the generator apparatus to cool the area electrodes as shown in FIG. 2 in accordance with the temperature distribution or preplanning thereof.

In view of these considerations, as will be appreciated by persons skilled in the art, implementations and systems should be considered broadly and with reference to the claims set forth below:

What is claimed is:

1. A system for inducing heat ablations in an operative field in patient's anatomy, which includes a volume of tissue to be ablated, comprising:
   at least one active plate electrode having an area greater than one square centimeter adapted to contact a first portion of tissue within the operative field;
   at least one reference electrode adapted to contact a second portion of tissue within the operative field, wherein the at least one plate electrode and the at least one reference electrode are cooperatively adapted and positioned to define a volume of tissue to be ablated within the patient's anatomy;
   a high frequency generator that generates an electrical output which when connected to the electrodes induces heating in the volume of tissue to induce an ablation of at least a portion of the volume of tissue; and
   at least one electrical coupling connecting the high frequency generator to the at least one plate electrode and the at least one reference electrode.

2. The system of claim 1 wherein the at least one plate electrode comprises one or more plates of conductive material.

3. The system of claim 1 wherein the at least one plate electrode comprises a surface of conductive metal.

4. The system of claim 1 wherein the at least one plate electrode comprises a conductive mesh of metal wires.

5. The system of claim 1 wherein the at least one plate electrode comprises an area of a plurality of conductive elements.

6. The system of claim 1 wherein the at least one plate electrode has a predetermined configuration suitable to conform the plate electrode to at least a portion of the first portion of tissue.

7. The system of claim 1 wherein the at least one plate electrode comprises at least one temperature sensor.

8. The system of claim 1 further comprising:
an imaging scanner to provide image representations of tissue within the operative field so as to monitor a position of the at least one plate electrode relative to the operative field.

9. The system of claim 1 further comprising:
a structure for grasping the at least one plate electrode and the at least one reference electrode to guide the at least one plate electrode and the at least one reference electrode in positions relative to a portion of tissue within the operative field such that the at least one plate electrode and the at least one reference electrode grasp the portion of tissue between them.

10. The system of claim 9 wherein the structure further comprises at least one hinge joint proximate the at least one plate electrode for adapting the at least one plate electrode to conform to a shape of a portion of the tissue.

11. The system of claim 1 wherein the at least one plate electrode comprises a fluid cooling system that cools at least a portion of the at least one plate electrode to prevent excessive heating of at least a portion of tissue within the operative field.

12. The system of claim 1 wherein the at least one plate electrode comprises a plurality of electrodes, which are configured to enable insertion into a portion of tissue within the operative field.

13. The system of claim 1 wherein the at least one plate electrode has an area between one square centimeter and fifty square centimeters.

14. The system of claim 1 wherein the at least one plate electrode has an area between one hundred square centimeter and one thousand square centimeters.

15. The system of claim 1 wherein the at least one plate electrode comprises a flexible material.

16. The system of claim 1 wherein the at least one plate electrode comprises a substrate with conductive elements.

17. The system of claim 1 wherein the at least one plate electrode comprises a mesh of conductors.

18. The system of claim 1 wherein the volume of tissue defines a tumor and the heating in the volume of tissue induces an ablation of at least a portion of the tumor.

19. A system for heat ablation of tissue within an operative field in a patient's anatomy, which includes a volume of tissue to be ablated, comprising:
at least two plate electrodes adapted to contact surface tissue of a portion of the patient's anatomy and each of the plate electrodes having an area of at least one square centimeter, wherein the at least two plate electrodes are cooperatively adapted and positioned to define a volume of tissue to be ablated within the patient's anatomy, at least one of the plate electrodes being an active electrode;
a high frequency generator that generates an electrical output which, when the at least two plate electrodes are in contact with the surface tissue within the operative field and when the electrical output is connected to the at least two plate electrodes, causes heating in the volume of tissue to induce an ablation of at least a portion of the volume of tissue; and
an electrical coupling of the generator to the at least two plate electrodes.

20. The system of claim 19 wherein the plate electrodes comprise one or more plates of conductive material.

21. The system of claim 19 wherein the plate electrodes comprise a surface of conductive metal.

22. The system of claim 19 wherein the plate electrodes comprise a conductive mesh of metal wires.

23. The system of claim 19 wherein the plate electrodes comprise an area of a plurality of conductive elements.

24. The system of claim 19 wherein the plate electrodes have predefined configurations suitable to conform to at least a portion of the surface tissue.

25. The system of claim 19 wherein the plate electrodes comprise at least one temperature sensor.

26. The system of claim 19 further comprising:
a structure for grasping the plate electrodes to enable at least a portion of the surface tissue to be grasped by the plate electrodes.

27. The system of claim 19 wherein the plate electrodes comprise a fluid cooling system that cools at least a portion of the plate electrodes.

28. The system of claim 19 wherein the volume of tissue defines a tumor and the heating in the volume of tissue induces an ablation of at least a portion of the tumor.

29. The system of claim 19 wherein at least one of the plate electrodes comprises a flexible material.

30. The system of claim 19 wherein at least one of the plate electrodes comprises a substrate with conductive elements.

31. The system of claim 19 wherein at least one of the plate electrodes comprises a mesh of conductors.

32. A process of heat ablation of a volume of tissue of a patient in an operative field, comprising the steps of:
disposing at least two plate electrodes each having an area greater than one square centimeter in contact with tissue within the operative field, wherein the at least two plate electrodes are cooperatively adapted and positioned to define a volume of tissue to be ablated within the operative field, at least one of the plate electrodes being an active electrode;
coupling the at least two plate electrodes to a high frequency generator; and
applying electrical output from the generator to the volume of tissue through the electrodes whereby to heat and ablate at least a portion of the volume of tissue.

33. The process of claim 32 further including the step of:
urging the plate electrodes against tissue within the operative field with a grasping structure which is adapted to force the electrodes toward one another and against the tissue within the operative field.

34. The process of claim 33 wherein the grasping structure comprises forceps with the electrodes coupled to the tongs of the forceps, and wherein the urging step comprises the step of applying a force on the forceps to close the electrodes together to press the electrodes against the tissue within the operative field.

35. The process of claim 32 wherein the plate electrodes comprise at least one temperature sensor, the process further comprising the step of:
monitoring at least one temperature of the tissue within the operative field by the at least one temperature sensor to control the heat ablation.

36. A system for inducing heat ablations in an operative field in a patient's anatomy, which includes tissue to be ablated, comprising:
at least one active plate electrode having an area greater than one square centimeter adapted to contact a portion of tissue proximate to a tissue volume within the operative field to be ablated, the at least one plate electrode comprising a mesh of conductors;

at least one reference electrode adapted to contact a portion of tissue proximate to a tissue volume within the operative field to be ablated;

a high frequency generator that generates an electrical output which when connected to the at least one plate electrode and the at least one reference electrode induces heating in the tissue volume and induces an ablation proximate the at least one plate electrode; and at least one electrical coupling connecting the high frequency generator to the at least one plate electrode and the at least one reference electrode.

37. The system of claim 36 wherein the at least one plate electrode comprises at least one temperature sensor.

38. The system of claim 37 wherein the at least one plate electrode further comprises a fluid cooling system that cools at least a portion of the at least one plate electrode to prevent excessive heating of at least a portion of tissue within the operative field.

39. The system of claim 36 wherein the at least one plate electrode comprises a fluid cooling system that cools at least a portion of the at least one plate electrode to prevent excessive heating of at least a portion of tissue within the operative field.

40. The system of claim 36 wherein the at least one plate electrode has a configuration suitable to conform the at least one plate electrode to a portion of tissue.

41. The system of claim 40 wherein the at least one plate electrode comprises at least one temperature sensor.

42. The system of claim 41 wherein the at least one plate electrode further comprises a fluid cooling system that cools at least a portion of the at least one plate electrode to prevent excessive heating of at least a portion of tissue within the operative field.

43. The system of claim 42 further comprising:

an imaging scanner to provide image representations of at least a portion of tissue and at least a portion of the at least one plate electrode within the operative field.

44. The system of claim 40 wherein the configuration is predetermined.

45. The system of claim 36 wherein the at least one reference electrode comprises at least one additional plate electrode having an area greater than one square centimeter.

46. The system of claim 36 further comprising:

a structure for grasping the at least one plate electrode and the at least one reference electrode to guide the at least one plate electrode and the at least one reference electrode in positions relative to a portion of tissue within the operative field such that the at least one plate electrode and the at least one reference electrode grasp a portion of tissue between them.

47. The system of claim 36 wherein the at least one plate electrode comprises a flexible material.

48. A system for inducing heat ablations in an operative field in a patient's anatomy, which includes tissue to be ablated, comprising:

at least one active plate electrode having an area greater than one square centimeter adapted to contact a portion of tissue proximate to a tissue volume within the operative field to be ablated, the at least one plate electrode comprising a fluid cooling system that cools at least a portion of the plate electrode to prevent excessive heating of a portion of tissue within the operative field;

at least one reference electrode adapted to contact a portion of tissue proximate to a tissue volume within the operative field to be ablated;

a high frequency generator that generates an electrical output which when connected to at least one plate electrode and the least one reference electrode induces heating in the tissue volume and induces an ablation proximate the at least one plate electrode; and at least one electrical coupling connecting the high frequency generator to the at least one plate electrode and the least one reference electrode.

49. The system of claim 48 wherein the at least one plate electrode comprises at least one temperature sensor.

50. The system of claim 49 wherein the at least one plate electrode further comprises a substrate with conductive elements.

51. The system of claim 49 wherein the at least one plate electrode has a configuration suitable to conform the at least one plate electrode to a portion of tissue.

52. The system of claim 51 further comprising:

an imaging scanner to provide image representations of at least a portion of tissue and at least a portion of the at least one plate electrode within the operative field.

53. The system of claim 48 wherein the at least one plate electrode has a configuration suitable to conform the at least one plate electrode to a portion of tissue.

54. The system of claim 53 wherein the at least one plate electrode further comprises a substrate with conductive elements.

55. The system of claim 53 wherein the configuration is predetermined.

56. The system of claim 48 wherein the at least one plate electrode comprises a mesh of conductors.

57. The system of claim 48 wherein the at least one plate electrode comprises a substrate with conductive elements.

58. The system of claim 48 further comprising:

an imaging scanner to provide image representations of at least a portion of tissue and at least a portion of the at least one plate electrode within the operative field.

59. The system of claim 48 wherein the at least one plate electrode comprises a flexible material.

60. The system of claim 48 wherein the at least one reference electrode comprises at least one additional plate electrode having an area greater than one square centimeter.

61. A method of heat ablation of tissue of a patient in an operative field, comprising the steps of:

disposing at least two plate electrodes each having an area greater than one square centimeter in contact with the tissue within the operative field near to the tissue to be ablated within the operative field, wherein at least one of the plate electrodes comprises a mesh of conductors, and is an active electrode;

coupling the at least two plate electrodes to a high frequency generator; and applying electrical output from the generator to the tissue to be ablated within the operative field through the electrodes whereby to heat and ablate the tissue to be ablated within the operative field.

62. A method of heat ablation of tissue of a patient in an operative field, comprising the steps of:

disposing at least two plate electrodes each having an area greater than one square centimeter in contact with the tissue within the operative field near to the tissue to be ablated within the operative field, wherein at least one of the plate electrodes is an active electrode and comprises a fluid cooling system that cools at least a portion of the at least one plate electrode to prevent excessive heating of a portion of tissue within the operative field;

coupling the at least two plate electrodes to a high frequency generator; and applying electrical output from the generator to the tissue to be ablated within the operative field through the electrodes whereby to heat and ablate the tissue to be ablated within the operative field.

* * * * *